US008568881B2

(12) United States Patent
Chandler et al.

(10) Patent No.: US 8,568,881 B2
(45) Date of Patent: *Oct. 29, 2013

(54) MAGNETIC MICROSPHERES FOR USE IN FLUORESCENCE-BASED APPLICATIONS

(71) Applicant: Luminex Corporation, Austin, TX (US)

(72) Inventors: Don J. Chandler, Austin, TX (US); Jason Bedre, Pflugerville, TX (US)

(73) Assignee: Luminex Corporation, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/648,015

(22) Filed: Oct. 9, 2012

(65) Prior Publication Data

US 2013/0095573 A1    Apr. 18, 2013

Related U.S. Application Data

(63) Continuation of application No. 12/731,290, filed on Mar. 25, 2010, now Pat. No. 8,283,037, which is a continuation of application No. 11/335,139, filed on Jan. 19, 2006, now Pat. No. 7,718,262.

(60) Provisional application No. 60/645,549, filed on Jan. 20, 2005.

(51) Int. Cl.
B32B 5/16    (2006.01)

(52) U.S. Cl.
USPC .......... 428/403; 428/404; 428/405; 428/406; 428/407; 428/842.1

(58) Field of Classification Search
USPC ..................... 428/402–407, 842.1
See application file for complete search history.

(56) References Cited

U.S. PATENT DOCUMENTS

| | | | |
|---|---|---|---|
| 5,032,381 A | 7/1991 | Bronstein et al. | 435/4 |
| 5,091,206 A | 2/1992 | Wang et al. | 427/2.18 |
| 5,283,079 A | 2/1994 | Wang et al. | 427/2.13 |
| 5,648,124 A | 7/1997 | Sutor | 427/475 |
| 5,736,330 A | 4/1998 | Fulton | 435/6.12 |
| 5,948,627 A | 9/1999 | Lee et al. | 435/7.24 |
| 5,981,180 A | 11/1999 | Chandler et al. | 435/6.12 |
| 6,013,531 A | 1/2000 | Wang et al. | 436/526 |
| 6,046,807 A | 4/2000 | Chandler | 356/318 |
| 6,139,800 A | 10/2000 | Chandler | 422/82.08 |
| 6,268,222 B1 | 7/2001 | Chandler et al. | 436/523 |
| 6,366,354 B1 | 4/2002 | Chandler | 356/318 |
| 6,411,904 B1 | 6/2002 | Chandler | 702/21 |
| 6,449,562 B1 | 9/2002 | Chandler | 702/19 |
| 6,514,295 B1 | 2/2003 | Chandler et al. | 8/607 |
| 6,524,793 B1 | 2/2003 | Chandler et al. | 435/6.12 |
| 6,592,822 B1 | 7/2003 | Chandler | 422/82.05 |
| 6,599,331 B2 | 7/2003 | Chandler et al. | 8/611 |
| 6,632,526 B1 | 10/2003 | Chandler | 428/402 |
| 6,929,859 B2 | 8/2005 | Chandler et al. | 428/403 |
| 6,939,720 B2 | 9/2005 | Chandler et al. | 436/518 |
| 7,718,262 B2 * | 5/2010 | Chandler et al. | 428/403 |
| 8,283,037 B2 * | 10/2012 | Chandler et al. | 428/403 |
| 2003/0186465 A1 | 10/2003 | Kraus et al. | 436/526 |
| 2006/0134775 A1 | 6/2006 | Phillips | 435/287.2 |

FOREIGN PATENT DOCUMENTS

| | | |
|---|---|---|
| GB | 2017125 | 10/1979 |
| JP | 2589618 | 12/1996 |
| JP | 2002-536285 | 10/2002 |
| JP | 2003-533363 | 11/2003 |
| WO | WO 91/09141 | 6/1991 |
| WO | WO 97/20214 | 6/1997 |

OTHER PUBLICATIONS

International Search Report issued in PCT Application No. PCT/US2006/002257, mailed Jun. 19, 2006.
Office Action issued in Chinese Patent Application No. 200680002382.5, mailed Jul. 4, 2008.
Office Action issued in Chinese Patent Application No. 200680002382.5, mailed Dec. 26, 2008.
Office Action issued in European Patent Application No. 06719207.0, mailed Aug. 22, 2008.
Office Communication issued in Japanese Patent Application No. 2007-552333, mailed Dec. 13, 2011 (English Translation).
U.S. Appl. No. 60/719,010, filed Sep. 21, 2005.
U.S. Appl. No. 11/305,805, filed Dec. 16, 2005.

* cited by examiner

*Primary Examiner* — Leszek Kiliman
(74) *Attorney, Agent, or Firm* — ParkerHighlander PLLC

(57) ABSTRACT

Microspheres, populations of microspheres, and methods for forming microspheres are provided. One microsphere configured to exhibit fluorescent and magnetic properties includes a core microsphere and a magnetic material coupled to a surface of the core microsphere. About 50% or less of the surface of the core microsphere is covered by the magnetic material. The microsphere also includes a polymer layer surrounding the magnetic material and the core microsphere. One population of microspheres configured to exhibit fluorescent and magnetic properties includes two or more subsets of microspheres. The two or more subsets of microspheres are configured to exhibit different fluorescent and/or magnetic properties. Individual microspheres in the two or more subsets are configured as described above.

23 Claims, 2 Drawing Sheets

MAGNETIC MICROSPHERES FOR USE IN FLUORESCENCE-BASED APPLICATIONS

PRIORITY APPLICATION

The present application is a continuation from prior U.S. patent application Ser. No. 12/731,290 filed Mar. 25, 2010 and which will issue as U.S. Pat. No. 8,283,037 on Oct. 9, 2012, which is a continuation from prior U.S. patent application Ser. No. 11/335,139 filed Jan. 19, 2006 and issued as U.S. Pat. No. 7,718,262 on May 18, 2010, which claims priority to U.S. Provisional Application No. 60/645,549 filed Jan. 20, 2005.

BACKGROUND OF THE INVENTION

1. Field of the Invention

The present invention generally relates to magnetic microspheres for use in fluorescence-based applications. Certain embodiments relate to a microsphere that includes a magnetic material coupled to a surface of a core microsphere and a polymer layer surrounding the magnetic material and the core microsphere.

2. Description of the Related Art

The following description and examples are not admitted to be prior art by virtue of their inclusion in this section.

Magnetic microspheres are currently used in a wide variety of applications, including: hyperthermic treatment of tumors; directed delivery of therapeutic substances to target locations in living systems; cell, polynucleotide, and protein isolation; and clinical analysis of biomolecules. Microspheres suitable for such purposes are available from a number of commercial sources in a number of different configurations. These microspheres often include a magnetically susceptible substance and a spherical matrix material such as an organic polymer or silica. The microspheres may have several configurations such as a magnetic core surrounded by a matrix; small magnetic particles dispersed throughout a matrix; and a magnetic coating on the outside of a spherical matrix. Each of these microsphere configurations has advantages and disadvantages, and selection of the appropriate configuration is dependent on the intended use of the microspheres.

For many purposes, appropriate microspheres display paramagnetism or superparamagnetism, rather than ferromagnetism. Such microspheres have negligible magnetism in the absence of a magnetic field, but application of a magnetic field induces alignment of the magnetic domains in the microspheres, resulting in attraction of the microspheres to the field source. When the field is removed, the magnetic domains return to a random orientation so there is no interparticle magnetic attraction or repulsion. In the case of superparamagnetism, this return to random orientation of the domains is nearly instantaneous, while paramagnetic materials will retain domain alignment for some period of time after removal of the magnetic field. This retention of domain alignment may lead to microsphere aggregation in the absence of an external magnetic field, which is often undesirable. Ferromagnetic materials have permanently aligned domains, so microspheres including such magnetic materials will readily aggregate.

The matrix material associated with the magnetic material also varies depending on the intended use of the microspheres, with silica and polymer latex being the most commonly used matrix materials. Both materials can be used to create substantially uniform magnetic microspheres in a wide range of diameters. Magnetic silica microspheres are often more stable over a wider range of temperatures than microspheres made from organic polymers such as polystyrene, and both materials may decompose in certain environments such as acidic or aromatic solvents. Additionally, silica microspheres are often more dense than latex microspheres, which can be an important consideration in the choice of magnetic microsphere matrices.

A significant and growing use of magnetic microspheres is in the field of biological assays. Assays for proteins and oligonucleotides can be performed on the surface of the microspheres, which can then be magnetically separated from the reaction mixture before the characteristics of the microspheres are measured. Isolation of the assay microspheres prior to measurement decreases interference of non-target molecules with the measurements thereby producing more accurate results.

Concurrent with the increasing interest in magnetic microspheres for biological assays is the development of assays conducted on fluorescent microspheres. The use of fluorescent labels or fluorescent material coupled to a surface of the microspheres or incorporated into the microspheres allows preparation of numerous sets of microspheres that are distinguishable based on different dye emission spectra and/or signal intensity. In a biological assay, the fluorescence and light scattering of these microspheres can be measured by a flow cytometer or an imaging system, and the measurement results can be used to determine the size and fluorescence of the microspheres as well as the fluorescence associated with the assay system being studied (e.g., a fluorescently labeled antibody in a "capture sandwich" assay), as described in U.S. Pat. No. 5,948,627 to Lee et al., which is incorporated by reference as if fully set forth herein. By varying the concentrations of multiple dyes incorporated in the microspheres, hundreds, or even thousands, of distinguishable microsphere sets can be produced. In an assay, each microsphere set can be associated with a different target thereby allowing numerous tests to be conducted for a single sample in a single container as described in U.S. Pat. No. 5,981,180 to Chandler et al., which is incorporated by reference as if fully set forth herein.

Fluorescently distinguishable microspheres may be improved by rendering these microspheres magnetically responsive. Examples of methods for forming fluorescent magnetic microspheres are described in U.S. Pat. No. 5,283,079 to Wang et al., which is incorporated by reference as if fully set forth herein. The methods described by Wang et al. include coating a fluorescent core microsphere with magnetite and additional polymer or mixing a core microsphere with magnetite, dye, and polymerizable monomers and initiating polymerization to produce a coated microsphere. These methods are relatively simple approaches to the synthesis of fluorescent magnetic microspheres, but are not suitable for creating the large numbers of precisely dyed microspheres used in relatively large multiplex assays such as those as described in U.S. Pat. No. 5,981,180 to Chandler et al.

This limitation of the methods of Wang et al. is due to the fact that most fluorescent dye molecules are extremely sensitive to attack by radical species generated during radical initiation polymerizations. If these radicals inactivate even a relatively small number of dye molecules, precise quantities of dye in the microspheres cannot be achieved. Furthermore, if the methods of Wang et al. are used to synthesize non-fluorescent magnetic microspheres, and dyeing of the microspheres is attempted using the solvent swelling method described in U.S. Pat. No. 6,514,295 to Chandler et al., which is incorporated by reference as if fully set forth herein, a relatively large amount of the magnetic material will be released from the microspheres during dyeing since the magnetic material is not chemically bound to the microspheres. In particular, physical entrapment of the magnetic material in the microspheres will be disrupted by the swelling process, and the magnetic material will be released into solution.

Fluorescent magnetic microspheres are also described in U.S. Pat. No. 6,268,222 to Chandler et al., which is incorporated by reference as if fully set forth herein. In this method, nanospheres are coupled to a polymeric core microsphere, and the fluorescent and magnetic materials are associated with either the core microsphere or the nanospheres. This method produces microspheres with desirable characteristics, but the nanosphere-microsphere bond may be susceptible to cleavage under severe reaction conditions. A coating surrounding the microsphere and nanospheres bound thereto may be used to improve this association but, again, the use of radical initiators to form this coating can compromise the fluorescent emission profile of the microsphere.

A more desirable configuration for a fluorescent magnetic microsphere is a magnetically responsive microsphere that can be dyed using established techniques, such as those described in U.S. Pat. No. 6,514,295 to Chandler et al. In general, this method uses solvents that swell the microsphere thereby allowing migration of the fluorescent material into the microsphere. These dyeing solvents include one or more organic solvents. Therefore, the microspheres must be able to tolerate organic solvents without losing their compositional integrity. Additionally, free magnetite interferes with a number of biological reactions. number of biological reactions. Therefore, microspheres that are susceptible to loss of even a relatively small amount of magnetite are unacceptable. As such, magnetic microspheres should be constructed such that the magnetic material is tightly bound to the microspheres thereby preventing loss of the magnetic material during the swelling process.

Magnetic microspheres are described in U.S. Pat. Nos. 5,091,206 to Wang et al., 5,648,124 to Sutor, and 6,013,531 to Wang et al., which are incorporated by reference as if fully set forth herein. However, the microspheres produced by the methods disclosed in these patents to Wang et al. may lose magnetic material when disposed in organic solvents since the magnetic material is not chemically immobilized. In each of these patents, substantially small particles of magnetic material are coated on a polymeric core microsphere, with a polymeric shell as an outer coating. The magnetic particles are synthesized and processed to minimize particle size. Some magnetic materials, such as $Fe_3O_4$, progress from ferromagnetic to paramagnetic to superparamagnetic as particle size decreases. Therefore, magnetite particles having the smallest size possible are used to faun the microspheres such that the product microsphere shows little magnetic retentivity.

However, if the product microsphere is also configured to emit a fluorescent signal from dye substances in the core microsphere, the thickness of the layer of magnetic particles on the surface of the microsphere core becomes an important consideration. For example, since most magnetic substances are optically opaque, a relatively thick coating of magnetic particles on the surface of the microsphere core will cause excessive light scatter or blocking of photon transmission. Using the methods of these patents, in which the magnetic component is designed to have the minimum particle size, magnetic content would have to be limited to allow light transmission through the magnetic component. In fact, to provide a magnetic microsphere having a diameter of 7 µm and 5% magnetic content, the entire surface of the core microsphere would have to be coated with a layer of magnetite having a thickness of 15 nm. This thickness results in a significantly lower fluorescent signal. Even if some of the fluorescent signal. Even if some of the magnetic particles are larger, as described by Sutor, the presence of a relatively large number of smaller magnetic particles will strongly impact the emission profile of the microsphere. One object of the invention of Sutor is to provide magnetically responsive microparticles having more electro magnetic units (EMUs) per gram of material than known microparticles.

The previously used methods also use surfactants and stabilizers in the preparation of the outer coatings. For many purposes, the presence of these molecules on the surface of the microsphere is acceptable. However, when used in bioassays, the surfactants can result in unwanted interference and changes in the binding efficiency of biomolecules to the microsphere surface. Washing procedures may reduce the quantity of surfactants and stabilizers associated with the microsphere surface, but completely removing the surfactants and stabilizers is extremely difficult.

Therefore, it would be a significant improvement over existing technologies to provide methods for forming a microsphere containing greater than about 2% by weight of a magnetically responsive material, without significantly hindering light transmission into and out of the microsphere. It would be a further improvement if this magnetically responsive material is strongly associated with the microsphere thereby reducing loss of the magnetically responsive material during dyeing and is surrounded by a polymer to substantially prevent the magnetically responsive material from interacting with biomolecules of interest. Furthermore, previously used methods can be improved if the outermost polymer layer is formed in the absence of surfactants and stabilizers.

SUMMARY OF THE INVENTION

The following description of various embodiments of microspheres, populations of microspheres, and methods for forming microspheres is not to be construed in any way as limiting the subject matter of the appended claims.

An embodiment relates to a microsphere configured to exhibit fluorescent and magnetic properties. The microsphere includes a core microsphere and a magnetic material coupled to a surface of the core microsphere. About 50% or less of the surface of the core microsphere is covered by the magnetic material. In addition, the microsphere includes a polymer layer surrounding the magnetic material and the core microsphere.

In one embodiment, the core microsphere includes one or more functional groups coupled to the surface of the core microsphere. In another embodiment, the microsphere includes one or more fluorochromes. In a different embodiment, the microsphere includes two or more different fluorochromes. In some embodiments, the fluorochrome(s) included in the microsphere are incorporated into the polymer layer as well as the core microsphere.

In some embodiments, the magnetic material includes particles having a size of about 10 nm to about 1000 nm. In a preferred embodiment, the magnetic material includes particles having a size of about 50 nm to about 300 nm. In some embodiments, the magnetic material includes single crystals of magnetite. In a further embodiment, the magnetic material includes aggregates of particles. For instance, the magnetic material may be aggregates of particles smaller than those described above such that the aggregates have a size in one of the above ranges. In another embodiment, the magnetic material includes a mixed metal magnetic material. In an additional embodiment, the microsphere includes one or more functional groups coupled to an outer surface of the polymer layer.

In one embodiment, the microsphere includes an additional magnetic material coupled to an outer surface of the polymer layer and an additional polymer layer surrounding the additional magnetic material. It will be easily recognized that alternating layers of magnetic material and polymer may be repeated in the microsphere until the desired magnetic content for the microsphere is achieved. In this manner, the microsphere may include one or more magnetic material/polymer layers, each of which is configured such that less than about 50% configured such that less than about 50% of the surface of the core microsphere is covered with magnetic material.

In one such embodiment, the magnetic material and the additional magnetic material have substantially the same composition. In a different embodiment, the magnetic material and the additional magnetic material have different compositions. In a further embodiment, at least one of the magnetic material and the additional magnetic material includes a mixed metal magnetic material. In another such embodiment, the polymer layer and the additional polymer layer are formed of substantially the same polymerizable material. In other embodiments, the polymer layer and the additional polymer layer are formed of different polymerizable materials. In some embodiments, the microsphere includes one or more functional groups coupled to an outer surface of the additional polymer layer. Each of the embodiments of the microsphere described above may be further configured as described herein and formed according to method embodiments described herein.

The microsphere embodiments described above provide several advantages over currently used microspheres having magnetic and fluorescent properties. For example, the microsphere described above can include greater than about 2% by weight of the magnetic material without significantly hindering light transmission into and out of the microsphere. In particular, it has been determined that when more than about 50% of the surface of the core microsphere is obscured by the magnetic material, the fluorescent emission of the microsphere becomes significantly impacted (i.e., the fluorescent emission is significantly lower). In addition, the magnetic material can be strongly associated with the microsphere as described further herein such that the magnetic material is not released from the microsphere during dyeing. The magnetized core microsphere is also coated with a polymer layer, which substantially prevents interaction between the magnetic material and biomolecules of interest. Furthermore, the polymer layer may be formed in the absence of surfactants and stabilizers.

Another embodiment relates to a population of microspheres configured to exhibit fluorescent and magnetic properties. The population includes two or more subsets of microspheres configured to exhibit different fluorescent properties, different magnetic properties, or different fluorescent and magnetic properties. Individual microspheres in the two or more subsets include a core microsphere and a magnetic material coupled to a surface of the core microsphere. About 50% or less of the surface of the core microsphere is covered by the magnetic material. The individual microspheres also include a polymer layer surrounding the magnetic material and the core microsphere. The individual microspheres and the population described above may be further configured as described herein.

An additional embodiment relates to a method for forming microspheres that exhibit magnetic properties. The method includes combining core microspheres with a magnetic material such that the magnetic material couples to a surface of the core microspheres to form magnetized core microspheres. About 50% or less of the surface of the core microspheres is covered by the magnetic material. The method also includes combining the magnetized core microspheres with one or more polymerizable materials such that the one or more polymerizable materials form a polymer layer surrounding the magnetized core microspheres thereby forming the microspheres that exhibit magnetic properties.

In one embodiment, the method includes separating magnetic particles by size into a first group and a second group. A substantial portion of the magnetic particles in the first group have a size of about 10 nm or greater. A substantial portion of the magnetic particles in the second group have a size of about 10 nm or lower. In one such embodiment, the magnetic material combined with the core microspheres includes the first group of magnetic particles. In another embodiment, the method includes combining the formed microspheres with an additional magnetic material such that the additional magnetic material couples to an outer surface of the polymer layer and forming an additional polymer layer surrounding the additional magnetic material.

In some embodiments, the method includes swelling the formed microspheres in a fluorochrome containing solvent such that the fluorochrome migrates into the formed microspheres. Such a method also includes changing one or more properties of the fluorochrome containing solvent such that the formed microspheres shrink thereby entrapping the fluorochrome in the formed microspheres. In a different embodiment, the method includes incorporating one or more fluorochromes into the core microspheres prior to combining the core microspheres with the magnetic material. In another embodiment, the method includes coupling one or more functional groups to an outer surface of the polymer layer. Each of the embodiments of the method described above may include any other step(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
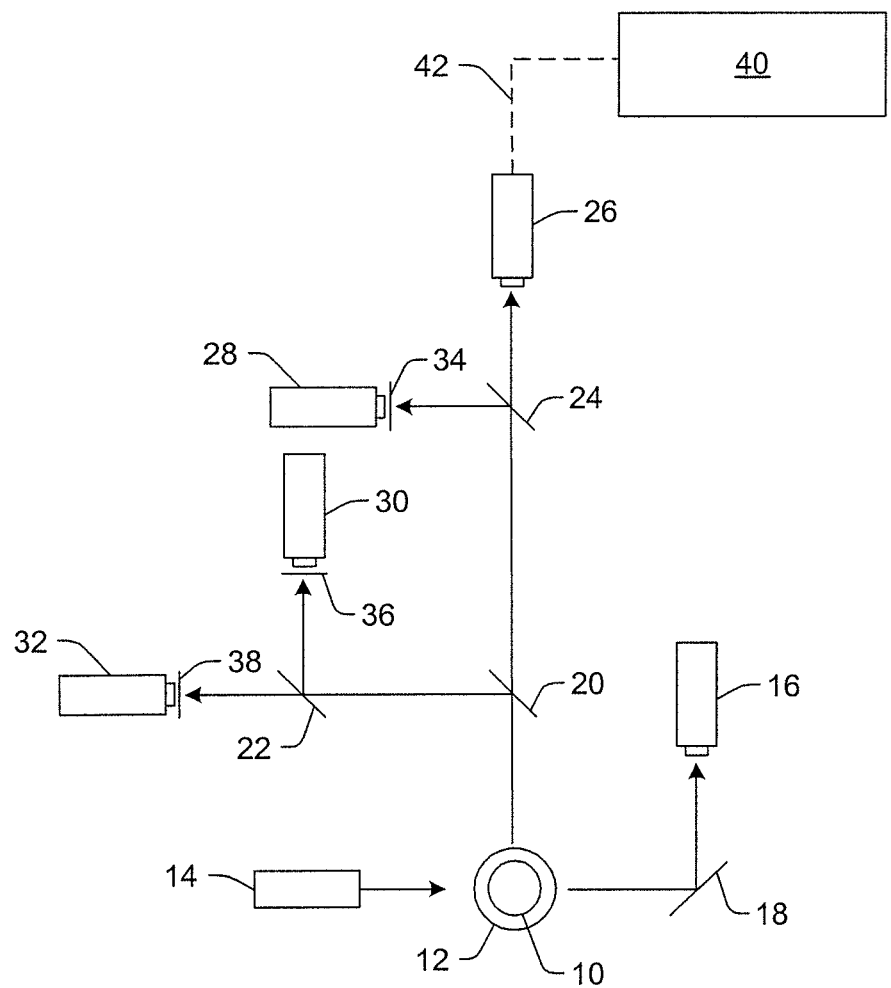
FIG. 1 is a schematic diagram illustrating one example of a system that may be used to perform measurements, experiments, and assays with the microsphere and population embodiments described herein.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular foam disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Microsphere embodiments described herein may serve as vehicles for molecular reactions. Examples of such molecular reactions and experiments, measurements, and assays in which the microsphere embodiments described herein may be used are described in U.S. Pat. Nos. 5,736,330 to Fulton, 5,981,180 to Chandler et al., 6,449,562 to Chandler et al., 6,524,793 to Chandler et al., 6,592,822 to Chandler, and 6,939,720 to Chandler et al., which are incorporated by reference as if fully set forth herein. The term "microsphere" as used herein is generally defined as a composite structure that may or may not be spherical in shape. The terms "microsphere," "particle," and "bead" are commonly used interchangeably by those of ordinary skill in the art. Therefore, the term "microsphere" as used herein may be replaced by the term "particle" or "bead" without altering the scope of the embodiments described herein.

FIG. 1 illustrates one example of a system that may be used to perform measurements, experiments, and assays with the microsphere and population embodiments described herein. It is noted that the figures described herein are not drawn to scale. In particular, the scale of some of the elements of the figures is greatly exaggerated to emphasize characteristics of the elements. In addition, the same reference numerals are used in the figures to indicate elements that may be similarly configured.

In FIG. 1, the system is shown along a plane through the cross-section of cuvette 12 through which microspheres 10 flow. The cuvette may be a quartz or fused silica cuvette such as that used in flow cytometers. Any other suitable type of viewing or delivery chamber, however, may also be used to deliver the sample for measurement. Microspheres 10 may be configured according to embodiments described herein.

The system includes light source 14. Light source 14 may include any appropriate light source known in the art such as a laser. The light source may be configured to emit light having one or more wavelengths such as blue light or green light. Light source 14 is configured to illuminate the microspheres as they flow through the cuvette. The illumination may cause the microspheres to emit fluorescent light having one or more wavelengths or wavelength bands. In some embodiments, the system may include one or more lenses (not shown) configured to focus light from the light source onto the microspheres or the flowpath. The system may also include more than one light source. In one embodiment, the light sources may be configured to illuminate the microspheres with light having different wavelengths or wavelength bands (e.g., blue light and green light). In some embodiments, the light sources may be configured to illuminate the microspheres at different directions.

Light scattered forwardly from the microspheres is directed to detection system 16 by folding mirror 18 or another suitable light directing component. Alternatively, detection system 16 may be placed directly in the path of the forwardly scattered light. In this manner, the folding mirror or other light directing components may not be included in the system. In in the system. In one embodiment, the forwardly scattered light is light scattered by the microspheres at an angle of about 180° from the direction of illumination by light source 14, as shown in FIG. 1. The angle of the forwardly scattered light may not be exactly 180° from the direction of illumination such that incident light from the light source may not impinge upon the photosensitive surface of the detection system. For example, the forwardly scattered light may be light scattered by the microspheres at angles less than or greater than 180° from the direction of illumination (e.g., light scattered at an angle of about 170°, about 175°, about 185°, or about 190°).

Light scattered by the microspheres at an angle of about 90° from the direction of illumination may also be collected. In one embodiment, this scattered light is separated into more than one beam of light by one or more beamsplitters or dichroic mirrors. For example, light scattered at an angle of about 90° to the direction of illumination may be separated into two different beams of light by beamsplitter 20. The two different beams of light may be separated again by beamsplitters 22 and 24 to produce four different beams of light. Each of the beams of light may be directed to a different detection system, which may include one or more detectors. For example, one of the four beams of light may be directed to detection system 26. Detection system 26 may be configured to detect light scattered by the microspheres.

Scattered light detected by detection system 16 and/or detection system 26 may generally be proportional to the volume of the microspheres that are illuminated by the light source. Therefore, output signals of detection system 16 and/or detection system 26 may be used to determine a diameter or size of the microspheres. In addition, the output signals of detection system 16 and/or detection system 26 may be used to identify more than one microsphere that are stuck together or that are passing through the illumination zone at approximately the same time. Therefore, such microspheres may be distinguished from other sample microspheres and calibration microspheres.

The other three beams of light may be directed to detection systems 28, 30, and 32. Detection systems 28, 30, and 32 may be configured to detect fluorescence emitted by the microspheres. Each of the detection systems may be configured to detect fluorescence of a different wavelength or a different range of wavelengths. For example, one of the detection systems may be configured to detect green fluorescence. Another of the detection systems may be configured to detect yellow-orange fluorescence, and the other detection system may be configured to detect red fluorescence.

In some embodiments, spectral filters 34, 36, and 38 are coupled to detection systems 28, 30, and 32, respectively. The spectral filters may be configured to block fluorescence of wavelengths other than that which the detection systems are configured to detect. In addition, one or more lenses (not shown) may be optically coupled to each of the detection systems. The lenses may be configured to focus the scattered light or emitted fluorescence onto a photosensitive surface of the detectors.

The detector's output current is proportional to the fluorescent light impinging on it and results in a current pulse. The current pulse may be converted to a voltage pulse, low pass filtered, and then digitized by an analog-to-digital (A/D) converter. Processor 40 such as a digital signal processor (DSP) integrates the area under the pulse to provide a number that represents the magnitude of the fluorescence. As shown in FIG. 1, processor 40 may be coupled to detection system 26 via transmission medium 42. Transmission medium 42 may include any appropriate transmission medium known in the art. Processor 40 may also be coupled to detection system 26 indirectly via transmission medium 42 and one or more other components (not shown) such as an A/D converter. The processor may be coupled to other detection systems of the system in a similar manner.

In some embodiments, the output signals that are responsive to fluorescence emitted by the microspheres are used to determine an identity of the microspheres and information about a reaction taking or taken place on the surface of the microspheres. For example, output For example, output signals of two of the detection systems may be used to determine an identity of the microspheres, and output signals of the other detection system may be used to determine a reaction taking or taken place on the surface of the microspheres. Therefore, the selection of the detection systems and the spectral filters may vary depending on the type of dyes incorporated into or bound to the microspheres and/or the reaction being measured (i.e., the dye(s) incorporated into or bound to the reactants involved in the reaction).

The detection systems that are used to determine an identity of the sample microspheres (e.g., detection systems 28 and 30) may be avalanche photodiodes (APDs), photomultiplier tubes (PMTS), or other photodetectors. The detection system that is used to identify a reaction taking or taken place on the surface of the microspheres (e.g., detection system 32) may be a PMT, an APD, or another form of photodetector. The system may be further configured as described herein.

Although the system of FIG. 1 is shown to include two detection systems having two different detection windows for distinguishing between microspheres having different dye characteristics, it is to be understood that the system may include more than two such detection windows (i.e., 3 detection windows, 4 detection windows, etc.). In such embodiments, the system may include additional beamsplitters and additional detection systems having other detection windows. In addition, spectral filters and/or lenses may be coupled to each of the additional detection systems.

In another embodiment, the system includes two or more detection systems configured to distinguish between different materials that are reacted on the surface of the microspheres. The different reactant materials may have dye characteristics that are different than the dye characteristics of the microspheres.

The system shown in FIG. 1 may also include a number of other components (not shown) that can be used to measure one or more magnetic properties of the microspheres. For example, the system may be configured to excite the microspheres magnetically as well as optically. The microspheres may be excited magnetically by applying an external magnetic field to the microspheres. The external magnetic field may be applied to the microspheres using any suitable device known in the art. The system may also include any appropriate magnetic detector known in the art that can be used to detect the magnetic field of the microspheres. The magnetic field caused by the induced magnetization of a microsphere that is detected by the magnetic detector is proportional to the magnetization of the microsphere, which is in turn proportional to the applied magnetic field. The detected magnetic fields of the microspheres can be used to determine an identity of the microspheres and/or a reaction taking or taken place on the surface of the microspheres.

Microspheres that exhibit measurable magnetic properties provide advantages over non-magnetic microspheres. For instance, the magnetic properties of the microspheres may be substantially stable over time particularly when the magnetic material is protected from exposure to other materials such as reagents (e.g., by a polymer layer as described herein) and since magnetic labels are not subject to photo-bleaching by the measurement systems. Furthermore, a substantial magnetic background is not usually present in a sample being analyzed using the microspheres. In this manner, the sample will not contribute to noise in the measurements of the magnetic properties of the microspheres. In addition, magnetic field application and detection are not blocked by aqueous reagents or biomaterials. Additionally, magnetism may be used to remotely manipulate the microspheres (e.g., for isolation of particular analytes in a sample). Moreover, a number of relatively sensitive magnetic field detection devices suitable for biotechnology applications are commercially available and can be incorporated into any of the systems described herein.

Additional examples of systems that may be used to perform measurements, experiments, and assays with microsphere and population embodiments described herein are illustrated in U.S. Pat. Nos. 5,981,180 to Chandler et al., 6,046,807 to Chandler, 6,139,800 to Chandler, 6,366,354 to Chandler, 6,411,904 to Chandler, 6,449,562 to Chandler et al., and 6,524,793 to Chandler et al., which are incorporated by reference as if fully set forth herein. The system described herein may be further configured as described in these patents. In addition, systems that can be used to perform measurements of microsphere and population embodiments described herein include systems described and illustrated in U.S. Patent Application Ser. Nos. 60/719,010 by Roth filed Sep. 21, 2005 and 11/305,805 by Phillips filed Dec. 16, 2005, which are incorporated by reference as if fully set forth herein. The systems described in these patents and patent applications may include components such as those described above such that the systems can measure one or more magnetic properties of the microspheres.

According to one embodiment, a method for forming microspheres that exhibit magnetic properties includes combining core microspheres with a magnetic material such that the magnetic material couples to a surface of the core microspheres to form magnetized (or "magnetically responsive") core microspheres. Core microspheres suitable for use in the embodiments described herein are available from a number of commercial sources and may be formed of any material that will bind to the selected magnetic material. The bond between the core microspheres and the magnetic material may be covalent, ionic, electrostatic, or any other suitable bond type known in the art. Some appropriate materials that can be used for core microspheres include, but are not limited to, polymers of styrene, divinyl benzene, silica, or acrylamide. The size of the core microspheres (e.g., a diameter in the case of spherical core microspheres) may be selected based on the measurement system and/or method in which the microspheres will be used. Appropriate sizes for core microspheres range from about 1 µm to about 100 µm in diameter, but other sizes will work as well. It is also noted that greater in diameter, but other sizes will work as well. It is also noted that greater uniformity in core microsphere size leads to more uniformity in dye (e.g., fluorescent dye or fluorophore) uptake and magnetic material binding.

In one embodiment, the core microspheres include one or more functional groups coupled to the surface of the core microspheres. Surface functionalities can be selected from a number of different reactive moieties such as amines, thiols, carboxylic acids, hydrazine, halides, alcohols, aldehydes, and any combination thereof. This list of functionalities is not meant to be a complete list of functionalities, and the microsphere functionalities may include any others known in the art. The one or more functional groups may be coupled to the surface of the core microspheres during formation of the core microspheres (e.g., by polymerization with one or more polymerizable materials that include one or more functional groups). Alternatively, the one or more functional groups may be attached to the surface of the core microspheres after the core microspheres have been formed. Such attachment of the one or more functional groups may be performed using any suitable method known in the art.

In one embodiment, combining core microspheres with a magnetic material as described above includes treating a solution of core microspheres with a solution containing a magnetically responsive material. In one embodiment, the method includes separating magnetic particles by size into a first group and a second group. A substantial portion of the magnetic particles in the first group have a size of about 10 nm or greater. A substantial portion of the magnetic particles in the second group have a size of about 10 nm or lower. In one such embodiment, the magnetic material combined with the core microspheres includes the first group of magnetic particles. In such an embodiment, the magnetic material combined with the core microspheres does not include the second group of magnetic particles. In this manner, the magnetically responsive material may be treated prior to treatment of the core microspheres to eliminate relatively fine particles from the solution that is used to treat the core microspheres.

Magnetic particle size selection can be performed, for example, by a partial acid digestion of the magnetic material (although this step is optional) followed by filtration or centrifugation to separate larger particles from smaller particles. The larger particles are retained for coupling to core microspheres, and the finer particles are discarded. It has been shown that repeated washing of the magnetic particles is advantageous since repeated washing more efficiently removes the finer particles from the bulk magnetite solution. Other methods that can be used to remove only the finer particles (e.g., particles smaller than about 10 nm or particles smaller than about 20 nm) can also be used to provide magnetic particles suitable for the embodiments described herein. The washed magnetic particles may then be re-suspended, preferably in an alcoholic solvent, prior to combination with the core microspheres. Alcoholic solvents are preferred for re-suspension since the reactivity of aqueous solvents and magnetic materials may generate hydroxides or other reduced species on the surface of the magnetic material, some of which are known to fluoresce, which would be undesirable for many applications in which the microsphere and population embodiments described herein may be used.

Some advantages of the embodiments described herein are provided by the processing of the magnetic material after its synthesis and prior to coupling to the core microspheres. Prior art methods such as those described in U.S. Pat. Nos. 5,283,079 to Wang et al. and 5,648,124 to Sutor, which are incorporated by reference as if fully set forth herein, use techniques to minimize particle size and isolate the finest particles. For example, the raw magnetite is often partially digested with an acid, and the magnetite is isolated from the solution by magnetic decantation, which retains all particle sizes, or by centrifugation and retention of the supernatant, which ensures retention of only the smallest particle sizes. However, the magnetic material used in the embodiments described herein preferably does not include such fine particles.

Substantially eliminating these smallest magnetic particles allows formation of a microsphere that has relatively high magnetite content while minimizing surface coverage of the core microsphere by the magnetic material. For example, if relatively small magnetic magnetic particles are coupled to the surface of the core microsphere, the particles effectively form a relatively thin layer across substantially the entire core microsphere surface resulting in a microsphere with low magnetic responsiveness and little ability for light emission from the core due to absorption of light by the particles. In one particular example, completely coating the surface of a 7 μm diameter microsphere with 5 nm diameter magnetite provides a microsphere with only 1% magnetite content. In addition, photon transmission into and out of this microsphere would be severely inhibited by the magnetite.

In a preferred embodiment, therefore, larger particles, or clusters (i.e., aggregates) of particles, are dispersed across the surface of the core microsphere such that the entire surface of the core microsphere is not covered by the magnetic particles. Therefore, the microsphere can have relatively high magnetic content due to the relatively large size of the particles and relatively high light transmission due to the partial surface coverage of the core microsphere by the magnetic particles. For example, by processing the magnetite to substantially exclude smaller particles and to retain particles or clusters having sizes in a range of about 10 nm to about 1000 nm, and more preferably about 50 nm to about 300 nm, it is possible to form a microsphere having about 5% magnetite content with only about 20% surface coverage of the core microsphere by the magnetic material. Microspheres formed according to embodiments described herein, therefore, advantageously have higher magnetic content and higher light transmission than magnetic microspheres formed by methods such as those disclosed by Wang et al. and Sutor, in which the object is to maximize magnetic content without regard to the degree of surface coverage or obstruction of light by the magnetic particles.

Figure 2:
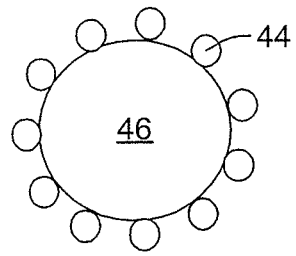
FIG. 2 is a schematic diagram illustrating a cross-sectional view of one embodiment of a magnetized core microsphere that includes a magnetic material coupled to a surface of a core microsphere.

Treating the core microspheres as described above produces magnetized core microspheres, which as shown in FIG. 2, include magnetic material 44 coupled to a surface of core microsphere 46. Preferably, about 50% or less of the surface of the core microsphere is covered by magnetic material 44. In other words, the magnetic material is coupled to only a portion of the surface of the core microsphere thereby resulting in partial coverage of the partial coverage of the surface by the magnetic material. Such coupling of the magnetic material to the core microsphere is advantageous since surface coverage of the core microsphere by the magnetic material exceeding about 50% has been shown to significantly impact (i.e., reduce) fluorescent emission from the fluorescently dyed core microsphere.

Magnetic material 44 may include particles. In one embodiment, magnetic material 44 includes particles having a size (e.g., a diameter) of about 10 nm to about 1000 nm. In a preferred embodiment, the magnetic material includes particles having a size of about 50 nm to about 300 nm. The size of the magnetic particles may be selected based on the size of the core microsphere, the selected surface coverage of the core microsphere by the magnetic particles, and the selected magnetic content of the microsphere. In general, the magnetic particles may have a size that is smaller than the size of the core microsphere such that multiple magnetic particles can be coupled to the surface of the core microsphere without complete coverage of the surface by the magnetic particles.

In some embodiments, the magnetic material includes single crystals of magnetite. In a different embodiment, the magnetic material includes aggregates of particles. The particles that form the aggregates may be smaller than the single crystals of magnetite. In addition, the particles that form the aggregates may have sizes such that the aggregates themselves have sizes in a range such as those described above. In a further embodiment, the magnetic material includes a mixed metal magnetic material.

The magnetic material may take a number of forms such as ferromagnetic, diamagnetic, paramagnetic, or super-paramagnetic. Of these forms, the last two are the most useful for embodiments described herein, and since super-paramagnetism is a subclass of paramagnetism, they will be treated the same in this discussion. A commonly used magnetic material is the iron oxide magnetite, $Fe_3O_4$. When such magnetite is prepared by methods that produce relatively small particle sizes, the magnetite is paramagnetic. One such method paramagnetic. One such method includes heating a solution of iron salts with a relatively strong base such as sodium hydroxide. One or more other divalent metals such as cobalt and manganese can be added to the iron salts to foam a mixed metal magnetic material with different properties. Many of these mixed metal compounds can be used to form magnetic microspheres. Other magnetic metal oxides are suitable for use in the embodiments described herein. Although some embodiments are described herein with respect to magnetite, any other appropriate magnetic material may be used in the embodiments described herein.

Figure 3:
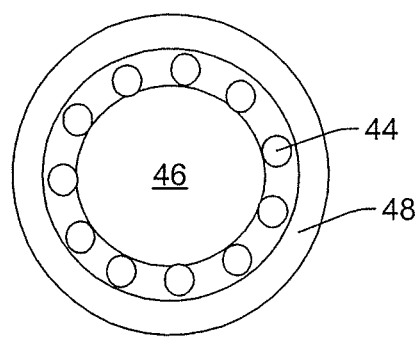
FIG. 3 is a schematic diagram illustrating a cross-sectional view of one embodiment of a microsphere that includes the magnetized core microsphere of FIG. 2 surrounded by a polymer layer.

The method embodiment also includes combining the magnetized core microspheres with one or more polymerizable materials such that the one or more polymerizable materials form a polymer layer surrounding the magnetized core microspheres thereby forming the microspheres that exhibit magnetic properties. For example, after coupling the magnetite to the surface of the core microsphere, a protective layer of polymer may be formed over the magnetized core microsphere. In this manner, the magnetically "coated" core microspheres are essentially coated with a polymeric material. The polymer layer may be configured to provide a barrier to prevent (or at least substantially reduce) contact of the magnetic material with the outer environment such as solvents, reactants, analytes, etc. that the formed microspheres may be exposed to in subsequent steps (e.g., dyeing) or during use (e.g., assays). For example, as shown in FIG. 3, polymer layer 48 surrounds magnetic material 44 and core microsphere 46. Although polymer layer 48 is shown in FIG. 3 as completely surrounding the magnetic material and the core microsphere, in practice the polymer layer may not completely surround the magnetized core microsphere. However, the polymer layer is preferably formed such that the polymer layer substantially prevents contact between the magnetic material and other materials that contact the outer surface of the polymer layer.

This polymer layer can be formed by suspending the magnetized core microspheres in a suitable solvent such as water or alcohol and adding to the suspension one or more monomers such as styrene, acrylic acid, or other suitable polymerizable molecules known in molecules known in the art along with a polymerization initiator and possibly other molecules as appropriate. It is preferable, although not required, that the monomer mixture includes a species capable of coordinating to the magnetite as well as being able to copolymerize with the other monomers such as, but not limited to, acrylic acid or vinyl pyridine. This coordination of the polymer layer to the magnetite will form a stronger coupling between the polymer layer and the magnetized core microsphere. The initiator can be a radical forming compound, a redox pair, or any other appropriate initiator known in the art. In the absence of an initiator, polymerization can be induced by any appropriate method known in the art such as ultrasonic or photochemical initiation. The polymer layer is preferably formed in the absence of surfactants and polymeric stabilizers, although this is not a requirement of the embodiments described herein.

As described above, one or more functional groups (not shown) may be coupled to the surface of core microsphere 46. In addition, or alternatively, the microspheres may include one or more functional groups (not shown) coupled to an outer surface of polymer layer 48. In particular, in some embodiments, the method includes coupling one or more functional groups to an outer surface of the polymer layer. The one or more functional groups may be coupled to the outer surface of the polymer layer during polymerization of the one or more polymerizable materials (e.g., by using one or more polymerizable materials that include one or more functional groups). Alternatively, the one or more functional groups may be attached to the outer surface of the polymer layer after the polymer layer has been formed. Such attachment may be performed using any suitable method known in the art. The one or more functional groups coupled to the outer surface of the polymer layer may include any of the functional groups described above. In addition, if one or more functional groups are coupled to the surface of the core microsphere and the outer surface of the polymer layer, the one or more functional groups coupled to the surface of the core microsphere may be substantially the same as or different than the one or more functional groups coupled to the outer surface of the polymer layer.

In one embodiment, the microspheres include one or more fluorochromes (not shown). In another embodiment, the microspheres include two or more different fluorochromes (not shown). Examples of suitable fluorochrome(s) for the microsphere embodiments described herein are described in the patents incorporated by reference herein. The fluorochrome(s) may be contained in the core microsphere, the polymer layer, or both the core microsphere and the polymer layer.

In one embodiment, the method includes incorporating one or more fluorochromes into the core microspheres prior to combining the core microspheres with the magnetic material. Therefore, the fluorochrome(s) are incorporated into the core microsphere before the polymer layer is formed. In addition, or alternatively, one or more fluorochromes may be attached to the surface of the core microsphere. The fluorochrome(s) may be attached to the surface of the core microsphere before the polymer layer is formed.

Additionally, or alternatively, fluorochrome(s) may be incorporated into the polymer layer and/or attached to the outer surface of the polymer layer. In this manner, the fluorochromes may be incorporated into the microsphere after the polymer layer is formed. The fluorochrome(s) incorporated into the polymer layer and/or attached to the outer surface of the polymer layer may be the same as or different than the fluorochrome(s) that are incorporated into the core microsphere and/or attached to the surface of the core microsphere. For example, different fluorochromes may be attached to the surface of the core microsphere and the outer surface of the polymer layer in different steps. In another example, the same fluorochrome(s) may be incorporated into the core microsphere and the polymer layer in the same step. The fluorochrome(s) may be incorporated into and/or attached to the surface of the core microsphere and/or the polymer layer using any appropriate method known in the art.

In one embodiment, the method includes swelling the formed microspheres in a fluorochrome containing solvent such that the fluorochrome migrates into the formed microspheres. Such a method also includes changing one or more properties of the fluorochrome containing solvent such that the formed microspheres shrink thereby entrapping the fluorochrome in the formed microspheres. Examples of methods that can be used for incorporating fluorochrome(s) into the microspheres as described above are illustrated in U.S. Pat. Nos. 6,514,295 to Chandler et al., 6,599,331 to Chandler et al., 6,632,526 to Chandler et al., and 6,929,859 to Chandler et al., which are incorporated by reference as if fully set forth herein. The fluorochrome containing solvent may include one or more fluorochromes or two or more different fluorochromes. The fluorochrome(s) may be entrapped in the core microspheres and possibly the polymer layer. For example, whether or not the fluorochrome(s) become entrapped in the polymer layer may vary depending on the characteristics of the fluorochromes(s) (which may be selected based on the characteristics of the core microspheres and the measurement systems and/or methods in which the formed microspheres will be used), the characteristics of the dyeing solvent, and the characteristics of the polymer layer.

Figure 4:
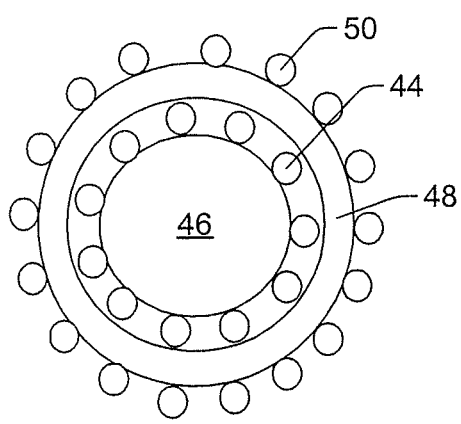
FIG. 4 is a schematic diagram illustrating a cross-sectional view of one embodiment of the microsphere of FIG. 3, which includes an additional magnetic material coupled to an outer surface of the polymer layer.
Figure 5:
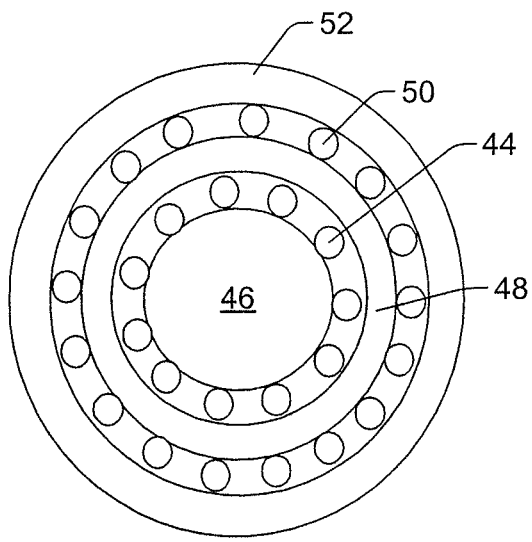
FIG. 5 is a schematic diagram illustrating a cross-sectional view of one embodiment of the microsphere of FIG. 4, which includes an additional polymer layer surrounding the additional magnetic material.

In some embodiments, the method includes combining the formed microspheres with an additional magnetic material such that the additional magnetic material couples to an outer surface of the polymer layer. Such an embodiment may also include forming an additional polymer layer surrounding the additional magnetic material. In one such embodiment, additional magnetic material 50 is coupled to an outer surface of polymer layer 48, as shown in FIG. 4. In such an embodiment, as shown in FIG. 5, additional polymer layer 52 may surround additional magnetic material 50. Polymer layer 52 may "surround" the additional magnetic material as described above. In this manner, the formed microspheres can optionally be coated with magnetic material 50 coupled to an outer surface of polymer layer 48, as shown in FIG. 4, followed by another polymeric coating (e.g., additional polymer layer 52 shown in FIG. 5), to increase the magnetic content of the formed microspheres. This process can be content of the formed microspheres. This process can be repeated as often as necessary to provide formed microspheres with the desired levels of light/fluorescence transmission and magnetic properties.

Magnetic material 50 may include any of the magnetic materials described above. Magnetic material 50 may also be formed as described above. In addition, magnetic materials 44 and 50 may have substantially the same composition or different compositions. Additional polymer layer 52 may be formed of any of the polymerizable materials described above. Additional polymer layer 52 may also be formed as described above. In addition, polymer layer 48 and additional polymer layer 52 may be formed of substantially the same polymerizable material or different polymerizable materials. Furthermore, as shown in FIGS. 4 and 5, the outer surface of polymer layer 48 is only partially covered by magnetic material 50. For example, about 50% or less of polymer layer 48 is covered by the additional magnetic material such that the light transmission/fluorescent emission properties of the formed microspheres are not substantially reduced by additional magnetic material 50.

As described above, one or more functional groups (not shown) may be coupled to the surface of core microsphere 46 and/or the outer surface of polymer layer 48. In addition, or alternatively, the microspheres may include one or more functional groups (not shown) coupled to an outer surface of additional polymer layer 52. In particular, in some embodiments, the method includes coupling one or more functional groups to an outer surface of the additional polymer layer. The one or more functional groups may be coupled to the outer surface of the additional polymer layer during polymerization of the one or more polymerizable materials (e.g., by using one or more polymerizable materials that include one or more functional groups). Alternatively, the one or more functional groups may be attached to the outer surface of the additional polymer layer after the additional polymer layer has been formed. Such attachment of the one or more functional groups may be performed using any appropriate method known in the art. The one or more functional groups coupled to the outer surface of the additional polymer layer may include any of the functional groups described include any of the functional groups described above. In addition, if one or more functional groups are coupled to the surface of the core microsphere and the outer surface of the additional polymer layer, the one or more functional groups coupled to the surface of the core microsphere may be substantially the same as or different than the one or more functional groups coupled to the outer surface of the additional polymer layer. If one or more functional groups are coupled to the outer surfaces of the polymer layer and the additional polymer layer, the one or more functional groups coupled to the outer surface of the polymer layer may be substantially the same as or different than the one or more functional groups coupled to the outer surface of the additional polymer layer.

As described above, fluorochrome(s) may be incorporated into the core microsphere and/or polymer layer 48 and/or may be attached to the surface of the core microsphere and/or the outer surface of polymer layer 48. Additionally, or alternatively, fluorochrome(s) may be incorporated into the additional polymer layer and/or attached to the outer surface of the additional polymer layer. The fluorochrome(s) incorporated into the additional polymer layer and/or attached to the outer surface of the additional polymer layer may be the same as or different than the fluorochrome(s) that are incorporated into the core microsphere and/or attached to the surface of the core microsphere. The fluorochrome(s) incorporated into the additional polymer layer and/or attached to the outer surface of the additional polymer layer may also be the same as or different than the fluorochrome(s) that are incorporated into the polymer layer and/or attached to the outer surface of the polymer layer. The fluorochrome(s) may be incorporated into and/or attached to the outer surface of the additional polymer layer using any appropriate method known in the art. Each of the embodiments of the method described above may include any other step(s) of any other method(s) described herein.

FIG. 3 illustrates one embodiment of a microsphere that is configured to exhibit fluorescent and magnetic properties. The microsphere includes core microsphere 46, which may be configured as described above. In one embodiment, the core microsphere includes one or more functional groups (not shown) coupled to the surface of the core microsphere. The microsphere. The one or more functional groups may include any of the functional groups described herein.

The microsphere also includes magnetic material 44 coupled to a surface of core microsphere 46. The magnetic material may include any of the magnetic materials described herein and may be configured as described herein. For example, in one embodiment, the magnetic material includes particles having a size (e.g., a diameter) of about 10 nm to about 1000 nm. In a preferred embodiment, the magnetic material includes particles having a size of about 50 nm to about 300 nm. In another embodiment, the magnetic material includes single crystals of magnetite. In a further embodiment, the magnetic material includes aggregates of particles. In some embodiments, the magnetic material includes a mixed metal magnetic material. Preferably, about 50% or less of the surface of the core microsphere is covered by the magnetic material.

The microsphere further includes polymer layer 48 surrounding the magnetic material and the core microsphere. The polymer layer may be configured as described above. In one embodiment, the microsphere includes one or more functional groups (not shown) coupled to an outer surface of the polymer layer. These one or more functional groups may include any of the functional groups described herein. In addition, if functional group(s) are coupled to the surface of the core microsphere and the outer surface of the polymer layer, the functional group(s) coupled to the surface of the core microsphere may be the same as or different than the functional group(s) coupled to the outer surface of the polymer layer.

In one embodiment, the microsphere includes an additional magnetic material coupled to an outer surface of the polymer layer and an additional polymer layer surrounding the additional magnetic material. For example, as shown in FIG. 5, the microsphere may include additional magnetic material 50 coupled to an outer surface of polymer layer 48 and additional polymer layer 52 surrounding the additional magnetic material. The additional magnetic material may include any of the magnetic materials described herein. In addition, the described herein. In addition, the additional magnetic material may be configured as described herein. For example, preferably, the combination of the magnetic material and the additional magnetic material covers about 50% or less of the surface of the core microsphere. In one embodiment, the magnetic material and the additional magnetic material have substantially the same composition. In an alternative embodiment, the magnetic material and the additional magnetic material have different compositions. In a further embodiment, at least one of the magnetic material and the additional magnetic material includes a mixed metal magnetic material.

Additional polymer layer 52 may be formed of any of the polymerizable materials described herein. In addition, the additional polymer layer may be configured as described herein. Furthermore, in one embodiment, the polymer layer and the additional polymer layer are formed of substantially the same polymerizable material. In an alternative embodiment, the polymer layer and the additional polymer layer are formed of different polymerizable materials.

In one embodiment, the microsphere includes one or more functional groups (not shown) coupled to an outer surface of the additional polymer layer. These one or more functional groups may include any of the functional groups described herein. In addition, if functional group(s) are coupled to the surface of the core microsphere and the outer surface of the additional polymer layer, the functional group(s) coupled to the surface of the core microsphere may be the same as or different than the functional group(s) coupled to the outer surface of the additional polymer layer. Furthermore, if functional group(s) are coupled to the outer surfaces of the polymer layer and the additional polymer layer, the functional group(s) coupled to the outer surface of the polymer layer may be the same as or different than the functional group(s) coupled to the outer surface of the additional polymer layer.

In some embodiments, the microsphere includes one or more fluorochromes. In another embodiment, the microsphere includes two or more different fluorochromes. For example, in one embodiment, one or more fluorochromes (not shown) or two or more different fluorochromes (not shown) may be coupled to a surface of the core microsphere and/or incorporated into the core microsphere. The fluorochrome(s) coupled to the surface of the core microsphere and/or incorporated into the core microsphere may include any of the fluorochromes described herein. In another embodiment, one or more fluorochromes (not shown) or two or more different fluorochromes (not shown) may be coupled to an outer surface of the polymer layer and/or incorporated into the polymer layer. The fluorochrome(s) coupled to the outer surface of the polymer layer and/or incorporated into the polymer layer may include any of the fluorochromes described herein. In a further embodiment, one or more fluorochromes (not shown) or two or more different fluorochromes (not shown) may be coupled to an outer surface of the additional polymer layer and/or incorporated into the additional polymer layer. The fluorochrome(s) coupled to the outer surface of the additional polymer layer and/or incorporated into the additional polymer layer may include any of the fluorochromes described herein. Furthermore, fluorochrome(s) may be attached to the surface of and/or incorporated into the core microsphere, the polymer layer, the additional polymer layer, or some combination thereof. Each of the embodiments of the microsphere described above may be further configured as described herein.

The microsphere embodiments described above provide several advantages over other currently used microspheres. For example, the microsphere described above can include greater than about 2% by weight of the magnetic material without significantly hindering light transmission into and out of the microsphere. In particular, it has been determined that when more than about 50% of the surface of the core microsphere is obscured by the magnetic material, the fluorescent emission of the microsphere becomes significantly impacted (i.e., the fluorescent emission is significantly lower). In addition, the magnetic material can be strongly associated with the surface of the core microsphere as described further herein such that the magnetic content of the microsphere is not reduced during dyeing operations. The magnetized reduced during dyeing operations. The magnetized core microsphere is also substantially surrounded by a polymer layer, which substantially prevents the magnetic material from interacting with the biomolecules of interest and other materials that contact the formed microsphere. Furthermore, the polymer layer may be formed in the absence of surfactants and stabilizers. Therefore, when the microsphere embodiments described herein are used in bioassays, unwanted interference and changes in the binding efficiency of biomolecules to the microsphere surface, which may be caused by surfactants and stabilizers, are eliminated. The microsphere embodiments described above also have all of the advantages of other embodiments described herein.

The microspheres described herein may be included in a population of microspheres configured to exhibit fluorescent and magnetic properties. For instance, one embodiment of a population of microspheres configured to exhibit fluorescent and magnetic properties includes two or more subsets of microspheres. The two or more subsets of microspheres are configured to exhibit different fluorescent properties, different magnetic properties, or different fluorescent and magnetic properties. The fluorescent and/or magnetic properties of the subsets are preferably sufficiently different across the subsets and sufficiently uniform within the subsets such that the fluorescent and/or magnetic properties, when measured, can be used to distinguish the subsets from each other (e.g., to determine the subset to which a microsphere belongs).

Individual microspheres in the two or more subsets may be configured as described herein. For instance, an individual microsphere includes a core microsphere. A magnetic material is coupled to a surface of the core microsphere. Preferably, about 50% or less of the surface of the core microsphere is covered by the magnetic material. The individual microsphere also includes a polymer layer surrounding the magnetic material and the core microsphere. The individual microspheres and the population may be further configured as described herein. This embodiment of a population of microspheres has all of the advantages of other embodiments described herein.

The following examples are not to be considered limiting embodiments of the invention and are included herein for example purposes only.

Example 1

Preparation of Magnetite 0.2 moles of Iron (III) chloride hexahydrate and 0.1 mole of iron (II) chloride tetrahydrate were dissolved in 400 ml of deionized water in a three-neck round bottom flask with overhead stirring. This mixture was heated to 90° C. with continued stirring. 520 ml of 6N NaOH was added dropwise over 1 hour. The reaction was allowed to continue for 24 hours.

Example 2

Magnetite and Polymer Coating 10.2 g of commercially available polystyrene core microspheres with a functionalized carboxylated surface modification were suspended in a total volume of 100 ml methanol. 12.4 ml of the prepared magnetite solution was washed with deionized water, followed by two washes in 1M HCL, and finally two washes with methanol. Each wash step was followed by centrifugation at approximately 4000×g to separate the larger magnetite particles from the smaller magnetic particles. The magnetite was resuspended in a total volume of 100 ml of methanol. The magnetite and the core microspheres were combined and allowed to mix for 3 hours. This mixture was then washed four times with deionized water, and then resuspended in a total volume of 375 ml of water and charged to a 500 ml three-neck round bottom flask. A mixture of 12.6 g distilled styrene, 0.768 g distilled divinylbenzene, 0.173 g benzoyl peroxide, and 1.47 g acrylic acid was prepared and charged to the 500 ml three-neck round bottom flask. The reaction mixture was then heated to 60° C. for 24 hours. The coated microspheres were washed with methanol, tetrahydrofuran, followed by three additional washes with methanol, once with water, and finally resuspended in deionized water.

Further modifications and alternative embodiments of various aspects of the invention may be apparent to those skilled in the art in view of this description. For example, microspheres and populations of microspheres that are configured to exhibit fluorescent and magnetic properties are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A microsphere comprising:
   (a) a core microsphere comprising a surface and an interior, wherein the surface comprises one or more functional groups and the interior comprises one or more fluorochromes; and
   (b) a magnetic material chemically coupled to the functional groups on the surface of the core microsphere, wherein 50% or less of the surface of the core microsphere is covered by the magnetic material.

2. The microsphere of claim 1, wherein the core microsphere comprises a polymer of styrene, divinyl benzene, silica, or acrylamide.

3. The microsphere of claim 1, wherein the one or more functional groups are selected from the group consisting of amines, thiols, carboxylic acids, hydrazine, halides, alcohols, and aldehydes.

4. The microsphere of claim 1, wherein the microsphere comprises only one fluorochrome.

5. The microsphere of claim 1, wherein the microsphere comprises two different fluorochromes.

6. The microsphere of claim 1, wherein the magnetic material is $Fe_3O_4$.

7. The microsphere of claim 1, wherein the microsphere further comprises a polymer layer surrounding the magnetic material and the core microsphere.

8. The microsphere of claim 7, wherein the polymer layer surrounding the magnetic material and the core microsphere comprises a polymer of styrene, divinyl benzene, silica, or acrylamide.

9. The microsphere of claim 1, wherein the magnetic material is chemically coupled to the functional groups on the surface of the core microsphere by a covalent bond.

10. The microsphere of claim 1, wherein the magnetic material is chemically coupled to the functional groups on the surface of the core microsphere by an ionic bond.

11. A microsphere comprising a surface and an interior, wherein a magnetic material and one or more fluorochromes are chemically coupled to the surface of the microsphere, wherein 50% or less of the surface of the microsphere is covered by the magnetic material.

12. The microsphere of claim 11, wherein the microsphere comprises a polymer of styrene, divinyl benzene, silica, or acrylamide.

13. The microsphere of claim 11, wherein the fluorochrome is coupled to the surface of the microsphere via a functional group selected from the group consisting of amines, thiols, carboxylic acids, hydrazine, halides, alcohols, and aldehydes.

14. The microsphere of claim 11, wherein the magnetic material is coupled to the surface of the microsphere via a functional group selected from the group consisting of amines, thiols, carboxylic acids, hydrazine, halides, alcohols, and aldehydes.

15. The microsphere of claim 11, wherein only one fluorochrome is coupled to the surface of the microsphere.

16. The microsphere of claim 11, wherein the microsphere comprises two different fluorochromes.

17. The microsphere of claim 11, wherein the magnetic material is $Fe_3O_4$.

18. The microsphere of claim 11, wherein the magnetic material is a mixed metal oxide.

19. The microsphere of claim 11, wherein the microsphere further comprises a polymer layer surrounding the magnetic material and the fluorochrome on the surface of the microsphere.

20. The microsphere of claim 19, wherein the polymer layer surrounding the magnetic material and the fluorochrome on the surface of the microsphere comprises a polymer of styrene, divinyl benzene, silica, or acrylamide.

21. The microsphere of claim 11, wherein the interior of the microsphere comprises one or more fluorochromes.

22. The microsphere of claim 11, wherein the magnetic material is chemically coupled to the surface of the core microsphere by a covalent bond.

23. The microsphere of claim 11, wherein the magnetic material is chemically coupled to the surface of the core microsphere by an ionic bond.

* * * * *